(12) United States Patent
Kahn et al.

(10) Patent No.: US 7,153,978 B2
(45) Date of Patent: Dec. 26, 2006

(54) METHOD FOR PURIFYING N-METHYL-2-PYRROLIDONE

(75) Inventors: Andrew P. Kahn, Eagleville, PA (US); Thomas W. Weir, Berwyn, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 513 days.

(21) Appl. No.: 10/791,982

(22) Filed: Mar. 3, 2004

(65) Prior Publication Data

US 2005/0197502 A1 Sep. 8, 2005

(51) Int. Cl.
*C07D 207/04* (2006.01)

(52) U.S. Cl. ...................................... 548/543; 548/541
(58) Field of Classification Search ................ 548/541, 548/543
See application file for complete search history.

(56) References Cited

U.S. PATENT DOCUMENTS

| | | | |
|---|---|---|---|
| 3,154,540 A | 10/1964 | Beer et al. ................ | 260/239.3 |
| 3,960,846 A | 6/1976 | Potin et al. ........... | 260/239.3 A |
| 4,008,289 A * | 2/1977 | Ward et al. .................. | 585/448 |
| 4,501,902 A | 2/1985 | Cleary ........................ | 548/555 |
| 4,837,338 A | 6/1989 | Krupay et al. .............. | 548/555 |
| 5,777,131 A | 7/1998 | Evans ........................ | 548/543 |
| 6,207,824 B1 | 3/2001 | Henkes et al. ............. | 540/451 |
| 6,217,771 B1 | 4/2001 | Boyle et al. ................ | 210/638 |
| 6,348,601 B1 | 2/2002 | Ohlbach et al. ............ | 548/552 |

* cited by examiner

*Primary Examiner*—Golam M. M. Shameem
(74) *Attorney, Agent, or Firm*—Jonathan L. Schuchardt

(57) ABSTRACT

A method for purifying N-methyl-2-pyrrolidone is disclosed. The method comprises treating N-methyl-2-pyrrolidone with an alumina that desorbs less than 100 μmol/g of isobutylene between 225° C. and 400° C. in a standard tert-butyl alcohol dehydration test. The method enables the removal of at least about 80% of amine impurities or at least about 60% of APHA color from the NMP at 4 bed volumes treated.

8 Claims, No Drawings

METHOD FOR PURIFYING N-METHYL-2-PYRROLIDONE

FIELD OF THE INVENTION

The invention relates to a method for purifying N-methyl-2-pyrrolidone. The method provides an improved way to remove color or amine impurities after manufacture.

BACKGROUND OF THE INVENTION

N-methyl-2-pyrrolidone (NMP) is a valuable solvent for paint strippers, graffiti removers, agricultural chemicals, floor polishes, automotive cleaners, industrial cleaners, and photoresist strippers. NMP is commonly manufactured by reacting methylamine with gamma-butyrolactone (see, e.g., U.S. Pat. No. 6,348,601). The most common way to purify NMP during the manufacturing process involves one or more distillation steps.

Even after manufacture, however, there is often a need to improve the quality of NMP, particularly for applications that require exceptionally high purity, such as electronics and pharmaceutical applications. Traces of amine impurities can remain in the NMP even after thorough distillation. Moreover, NMP can develop undesirable color upon prolonged storage, particularly if the solvent contains traces of acids, amines, or other impurities.

Amine-contaminated NMP has been purified with gel-type and macroporous cation exchangers (see U.S. Pat. Nos. 5,777,131 and 6,207,824). Basic ion-exchange resins have been used to remove acidic impurities from NMP when the NMP was used as an extraction solvent and required purification thereafter (see U.S. Pat. No. 6,217,771). U.S. Pat. No. 4,501,902 describes another process for removing acidic impurities from contaminated NMP with a solid inorganic compound, which could be "alumina." A water-washed, activated alumina was used to purify NMP after the NMP was used to extract aromatic compounds from lubricating oil distillates (see U.S. Pat. No. 4,837,338).

In sum, aluminas have only infrequently been proposed for purifying NMP, and even then, they have generally been used to purify NMP that has been contaminated with impurities from a washing or extraction process. Little is known about the potential benefits of purifying NMP immediately post-manufacture with aluminas. Even less is known about how to select aluminas that will afford the greatest benefit in eliminating amine impurities and reducing color.

SUMMARY OF THE INVENTION

The invention is a method for purifying N-methyl-2-pyrrolidone (NMP), preferably NMP that has APHA color or contains amine impurities. The method comprises treating NMP with an alumina that desorbs less than 100 µmol/g of isobutylene between 225° C. and 400° C. in a standard tert-butyl alcohol dehydration test as described herein. We surprisingly found that the method enables removal of at least about 80% of amine impurities or at least about 60% of APHA color from the NMP at 4 bed volumes treated.

DETAILED DESCRIPTION OF THE INVENTION

N-Methyl-2-pyrrolidone (NMP) treated by the method of the invention comes from any suitable source. Preferably, however the NMP contains unacceptable levels of APHA color or amine impurities. The method is particularly valuable for treating recently manufactured NMP, especially NMP made by reacting methylamine with gamma-butyrolactone. It can also be used to treat NMP that has developed color upon storage or become contaminated through its use as a solvent or cleaner. The method can be used to complement a distillation process for purifying NMP. In sum, the origin of the NMP treated by the method of the invention is not believed to be critical.

The method comprises treating the NMP with an alumina. Not all aluminas are suitable for use in practicing the method. Suitable aluminas are those capable of desorbing less than 100 µmol/g of isobutylene between 225° C. and 400° C. in a standard tert-butyl alcohol (TBA) dehydration test as described herein (see examples below). Preferably, the alumina can desorb less than 50 µmol/g of isobutylene, and most preferably less than 10 µmol/g of isobutylene. Suitable aluminas include, for example, Alcoa Selexsorb CDX, Engelhard 5545, Axens CA 2/5, Axens SAS 870, and the like, and mixtures thereof. Aluminas not suitable for use, based on the TBA dehydration results, are Alcoa SCT 2551, Alcoa SCT-H 40103, and the like. These are unsuitable because they desorb at least 100 µmol/g of isobutylene in the required temperature range in the standard test.

In one aspect, the method is performed under conditions effective to remove at least 80%, and preferably at least 95%, of amine impurities from the N-methyl-2-pyrrolidone at 4 bed volumes of NMP treated. Thus, at the end of the fourth bed volume of NMP, the alumina should still be removing at least 80% of the amine impurities from the NMP. The initial and final levels of amine impurities in a sample can be determined by any suitable means, including gas chromatography, chemical analysis, titration, or other techniques. In one convenient approach, the level of amine impurities is determined by titration with a standardized solution of hydrochloric acid.

In another aspect, the method is performed under conditions effective to remove at least 60%, and preferably at least 65%, of the APHA color from the N-methyl-2-pyrrolidone at 4 bed volumes of NMP treated. The initial and final APHA color values are determined by visual comparison with standards according to ASTM method D 1209.

The invention is conveniently practiced by passing a feed stream of N-methyl-2-pyrrolidone through a column packed with a suitable grade of alumina at a relatively constant rate. Preferably, the liquid hourly space velocity (LHSV) ranges from about 0.25/h to about 20/h and more preferably from about 1/h to about 10/h. Color and/or amine impurity removal are usually monitored by periodic sampling and analysis to ensure that the treated NMP meets the desired product specifications. In one approach, the NMP to be treated is pumped into the bottom portion of the column and flows upwardly to an exit at the top of the column. In another suitable approach, the liquid flows downward by gravity through the column, with or without application of air or inert gas pressure at the top of the column. See Example 1 for one suitable approach.

After use, the alumina can be regenerated by methods that are well known in the art, including calcination, washing, or a combination of these techniques. Preferably, calcination is performed in air or under nitrogen at a temperature within the range of about 120° C. to about 500° C. Suitable wash solvents include, for example, alcohols, esters, ketones, water, or the like, and mixtures thereof. Methanol, water, and mixtures thereof are preferred.

The following examples merely illustrate the invention. Those skilled in the art will recognize many variations that are within the spirit of the invention and scope of the claims.

EXAMPLES 1–6 AND COMPARATIVE EXAMPLES 7–8

Removal of Color and Amine Impurities from NMP

Example 1

A one-cm ID column is packed with a sample of Alcoa Selexsorb CDX alumina (63.9 g, 100 cm$^3$). A feed of N-methyl-2-pyrrolidone that contains 13.7 ppm of amine impurities and has an APHA color of 18.9 is passed upwardly through the column at 200 mL/h. The product is collected in aliquots (200 mL) and checked for color (ASTM method D1209) and amine content (by titration with hydrochloric acid).

| Aliquot# | Bed Vols Treated | % Amines Removed | % Color Reduced |
|---|---|---|---|
| 1 | 2 | 97 | 71 |
| 2 | 4 | 96 | 69 |
| 3 | 6 | 93 | 70 |
| 4 | 8 | 94 | 66 |
| 5 | 10 | 92 | 65 |
| 6 | 12 | 93 | 63 |

Example 2

The procedure of Example 1 is followed using Engelhard 5545 alumina (61.6 g, 100 cm$^3$) and a feed that contains 10.4 ppm of amine impurities and has an APHA color of 29.4. The feed is passed upwardly through the column at 400 mL/h and aliquots (400 mL) are collected and analyzed for amine content and APHA color. The following results are obtained:

| Aliquot# | Bed Vols Treated | % Amines Removed | % Color Reduced |
|---|---|---|---|
| 1 | 4 | 96 | 72 |
| 2 | 8 | 92 | 71 |
| 3 | 12 | 90 | 71 |
| 4 | 16 | 89 | 69 |

Example 3

The procedure of Example 1 is followed using Axens SAS 870 alumina (57.9 g, 100 cm$^3$) and a feed that contains 14.0 ppm of amine impurities and has an APHA color of 17.0. The following results are obtained:

| Aliquot# | Bed Vols Treated | % Amines Removed | % Color Reduced |
|---|---|---|---|
| 1 | 2 | 99 | 86 |
| 2 | 4 | 97 | 68 |
| 3 | 6 | 93 | 62 |
| 4 | 8 | 93 | 61 |
| 5 | 10 | 93 | 54 |
| 6 | 12 | 93 | 48 |

Example 4

The procedure of Example 1 is followed using Axens CA 2/5 alumina (61.5 g, 100 cm$^3$) and a feed that contains 16.1 ppm of amine impurities and has an APHA color of 17.3. The following results are obtained:

| Aliquot# | Bed Vols Treated | % Amines Removed | % Color Reduced |
|---|---|---|---|
| 1 | 2 | 99 | 54 |
| 2 | 4 | 99 | 64 |
| 3 | 6 | 94 | 64 |
| 4 | 8 | 94 | 66 |
| 5 | 10 | 94 | 64 |
| 6 | 12 | 92 | 62 |

Example 5

The procedure of Example 1 is followed using Alcoa DD470 alumina (53.7 g, 100 cm$^3$) and a feed that contains 16.1 ppm of amine impurities and has an APHA color of 17.3. The following results are obtained:

| Aliquot# | Bed Vols Treated | % Amines Removed | % Color Reduced |
|---|---|---|---|
| 1 | 2 | 94 | 66 |
| 2 | 4 | 88 | 62 |
| 3 | 6 | 88 | 55 |
| 4 | 8 | 81 | 42 |
| 5 | 10 | 75 | 31 |
| 6 | 12 | 73 | 24 |

Example 6

The procedure of Example 1 is followed using Porocel 2PA 0159 alumina (51.7 g, 100 cm$^3$) and a feed that contains 16.1 ppm of amine impurities and has an APHA color of 17.3. The following results are obtained:

| Aliquot# | Bed Vols Treated | % Amines Removed | % Color Reduced |
|---|---|---|---|
| 1 | 2 | 92 | 61 |
| 2 | 4 | 86 | 61 |
| 3 | 6 | 73 | 51 |
| 4 | 8 | 68 | 47 |
| 5 | 10 | 65 | 38 |
| 6 | 12 | 65 | 27 |

Comparative Example 7

The procedure of Example 1 is followed using Alcoa SCT 2551 alumina (55.6 g, 100 cm$^3$) and a feed that contains 16.1 ppm of amine impurities and has an APHA color of 17.3. The following results are obtained:

| Aliquot# | Bed Vols Treated | % Amines Removed | % Color Reduced |
|---|---|---|---|
| 1 | 2 | 63 | 50 |
| 2 | 4 | 48 | 48 |
| 3 | 6 | 50 | 45 |
| 4 | 8 | 50 | 39 |
| 5 | 10 | 50 | 32 |
| 6 | 12 | 50 | 29 |

Comparative Example 8

The procedure of Example 1 is followed using Alcoa SCT-H 40103 alumina (65.5 g, 100 cm$^3$) and a feed that contains 16.1 ppm of amine impurities and has an APHA color of 17.3. The following results are obtained:

| Aliquot# | Bed Vols Treated | % Amines Removed | % Color Reduced |
|---|---|---|---|
| 1 | 2 | 36 | 28 |
| 2 | 4 | 36 | 38 |
| 3 | 6 | 36 | 41 |
| 4 | 8 | 33 | 35 |
| 5 | 10 | 29 | 31 |
| 6 | 12 | 29 | 23 |

Standard TBA Dehydration Test

Briefly, the test involves drying an alumina sample, saturating acid sites on the alumina with adsorbed tert-butyl alcohol (TBA), and temperature-programmed desorption coupled with analysis by mass spectrometry.

Alumina samples are first ground to a fine powder to eliminate diffusion effects. The amount of alumina used is adjusted to provide a total desorption of TBA of about 0.5 mg. Thus, an alumina sample (10–20 mg) is dried under high vacuum (10$^{-5}$ mm Hg) at 400° C. to constant weight for about 1 h. The sample is then exposed to TBA at 35° C. and 25 mm Hg until a constant weight is observed. Excess volatile material is pumped away under high vacuum (10$^{-5}$ mm Hg). The remaining TBA (typically 0.4 to 0.8 mg) is strongly adsorbed. The temperature of the sample is then increased at 5° C./min. to 400° C. The change in mass as a function of time is monitored to measure the amount of desorbing material. Additionally, mass spectrometric analysis is used to monitor compositional changes in the desorbed material. The result is a data set with weight loss and associated compounds as a function of temperature. For each alumina sample tested, the amount of isobutylene desorbed at 225–400° C. in µmoles per gram is reported in Table 1.

We unexpectedly found that isobutylene desorption in the 225–400° C. range correlates remarkably well with amine removal and color removal from N-methyl-2-pyrrolidone. In particular, aluminas useful in the invention desorb less than 100 µmol/g of isobutylene between 225° C. and 400° C. in the standard TBA dehydration test. Such aluminas were capable of removing (at 4 bed volumes treated) at least about 80% of the amine impurities or at least about 60% of the APHA color from the N-methyl-2-pyrrolidone.

Interestingly, other possible ways of predicting amine and APHA color removal capability of aluminas were not illuminating. For example, neither color removal nor amine removal correlated with the surface area of the alumina. Additionally, even isopropylamine (IPA) adsorption capacity did not correlate well either color or amine removal; for example, Alcoa SCT 2551 can adsorb a relatively high amount isopropylamine, but it is relatively poor for removing amines or APHA color from N-methyl-2-pyrrolidone; conversely, Engelhard 5545 can adsorb relatively little IPA, but it performs well in removing both color and amine impurities from NMP. The number of acid sites per surface area (based on IPA adsorbance) also did not correlate with amine removal or color removal. For example, Alcoa SCT 2551 and Alcoa Selexsorb CDX both had acid site/surface area values of about 1.8 µmol/m$^2$, but only the latter performed well in removing APHA color and amines from NMP.

The preceding examples are meant only as illustrations. The following claims define the invention.

TABLE 1

Effect of Alumina Selection on Amine and Color Removal from N-Methyl-2-Pyrrolidone

| Ex | Supplier | Alumina | Surface area (m$^2$/g) | IPA adsorbed (µmol) | Acid sites/SA (IPA) (µmol/m$^2$) | Isobutylene desorbed at 225–400° C. (µmol/g) | % Removal at 4 bed volumes treated | | Overall rating |
|---|---|---|---|---|---|---|---|---|---|
| | | | | | | | Amines | APHA color | |
| 1 | Alcoa | Selexsorb CDX | 460 | 836 | 1.82 | 0 | 96 | 69 | good |
| 2 | Engelhard | 5545 | 220 | 343 | 1.56 | 0 | 96 | 72 | good |
| 3 | Axens | SAS 870 | 241 | 408 | 1.69 | 9 | 97 | 68 | good |
| 4 | Axens | CA 2/5 | 342 | 743 | 2.17 | 41 | 99 | 64 | good |
| 5 | Alcoa | DD470 | 261 | 499 | 1.91 | 46 | 88 | 62 | fair |
| 6 | Porocel | 2PA 0159 | 268 | 449 | 1.68 | 96 | 86 | 61 | fair |
| C7* | Alcoa | SCT 2551 | 372 | 683 | 1.84 | 151 | 48 | 48 | poor |
| C8* | Alcoa | SCT-H 40103 | 293 | 236 | 0.81 | 191 | 36 | 38 | poor |

*Comparative examples

We claim:

1. A method which comprises treating N-methyl-2-pyrrolidone with an alumina that desorbs less than 100 μmol/g of isobutylene between 225° C. and 400° C. in a standard tert-butyl alcohol dehydration test as described herein.

2. The method of claim 1 wherein the alumina desorbs less than 50 μmol/g of isobutylene.

3. The method of claim 1 wherein the alumina desorbs less than 10 μmol/g of isobutylene.

4. The method of claim 1 performed under conditions effective to remove at least about 80% of amine impurities from the N-methyl-2-pyrrolidone at 4 bed volumes treated.

5. The method of claim 4 performed under conditions effective to remove at least about 95% of the amine impurities.

6. The method of claim 1 performed under conditions effective to remove at least about 60% of APHA color from the N-methyl-2-pyrrolidone at 4 bed volumes treated.

7. The method of claim 6 performed under conditions effective to remove at least about 65% of the APHA color.

8. The method of claim 1 wherein the alumina is selected from the group consisting of Alcoa Selexsorb CDX, Engelhard 5545, Axens CA 2/5, and Axens SAS 870.

* * * * *